United States Patent
Xianbin et al.

(12) 
(10) Patent No.: US 6,576,230 B1
(45) Date of Patent: Jun. 10, 2003

(54) BIOCIDAL MIXTURE OF 2-PROPENAL-RELEASING POLYMER AND ISOTHIAZOLONES

(75) Inventors: Liu Xianbin, Basking Ridge, NJ (US); Karen Winkowski, Sayreville, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/975,880

(22) Filed: Oct. 11, 2001

(51) Int. Cl.[7] ................................................ A61K 31/74
(52) U.S. Cl. ................................ 424/78.31; 424/78.08; 514/372; 526/315
(58) Field of Search .................... 514/372; 526/315; 424/78.08, 78.31

(56) References Cited

U.S. PATENT DOCUMENTS

| | | | | |
|---|---|---|---|---|
| 4,725,611 A | | 2/1988 | Mahn et al. ................. | 514/372 |
| 4,906,651 A | * | 3/1990 | Hsu ........................... | 514/372 |
| 4,980,176 A | | 12/1990 | Berke et al. ................. | 424/682 |
| 5,142,058 A | | 8/1992 | Willingham et al. ........ | 548/213 |
| 5,210,094 A | | 5/1993 | Reeve ........................ | 514/372 |
| 5,356,952 A | | 10/1994 | Schmidt ..................... | 523/122 |
| 6,060,571 A | * | 5/2000 | Werle et al. ................. | 526/315 |
| 6,114,366 A | | 9/2000 | Lutz et al. ................... | 514/372 |
| 6,211,213 B1 | | 4/2001 | El A'mma ................... | 514/372 |

* cited by examiner

Primary Examiner—Jose' G. Dees
Assistant Examiner—Konata M George
(74) Attorney, Agent, or Firm—Abelman, Frayne & Schwab

(57) ABSTRACT

A synergistic biocidal composition comprising a mixture of 2-propenal polymer (APC) and 5-chloro-2-methyl-4-isothiazoline-3-one (CIT) and 2-methyl-4-isothiazoline-3-one (MIT).

4 Claims, No Drawings

BIOCIDAL MIXTURE OF 2-PROPENAL-RELEASING POLYMER AND ISOTHIAZOLONES

FIELD OF THE INVENTION

The present invention relates to an antimicrobial composition comprising a mixture of a 2-propenal-releasing polymer and isothiazolones.

BACKGROUND OF THE INVENTION

Water-containing formulations and substrates, for example, paints and coating formulations, latex emulsions, inks, adhesives, sealants, joint compounds and concrete, are susceptible to microbial attack when exposed to common environmental conditions. Organisms causing spoilage or defacement include bacteria, yeast, fungi and algae. These microorganisms may degrade or impair different properties and attributes of such formulations and substrates by affecting their pH, viscosity, color, odor and rheology, among others.

The use of biocides to protect these formulations and substrates is of paramount importance. There are continuous efforts being made to develop more effective, less toxic and more economical biocides. Synergistic mixtures provide many of these desirable attributes.

Synergistic antimicrobial activity exists when the combination of two or more antimicrobial compounds results in the use of lesser amounts of each, to bring about the same inhibitory effect than the use of either compound acting alone. The synergistic interaction thus produces an effect that is more than additive in the resultant antimicrobial activity.

The compound 2-propenal polymer or copolymer is disclosed in U.S. Pat. No. 6,060,571 as being useful in aqueous systems as a biocide and is available commercially as NUOSEPT APC from Degussa. Its antimicrobial activity is linked to the release of free monomeric 2-propenal. 2-propenal polymer (APC) is a broad-spectrum biocide used to protect various products including aqueous dispersions, emulsion paint coatings, polymers for latices, amine-free cutting oils and cooling water circuits. It is an effective biocide against various bacteria, yeast and algae.

Isothiazolones such as the mixture of 5-chloro-2-methyl4-isothiazoline-3-one and 2-methyl-4-isothiazoline-3-one (CIT/MIT) is also commercially available (Kathon LX 1.5, from Rohm & Haas). Isothiazolones are disclosed in U.S. Pat. Nos. 3,761,488; 4,105,431; 4,252,694; 4,265,899; 4,279,762 and elsewhere. Mixtures of CIT/MIT have been used to preserve personal care, household and industrial products and show good microbiocidal activity.

The use of antimicrobial compositions which evidence synergistic activities present several advantages: an increase in effectiveness, a broadened antimicrobial spectrum of activity, a reduction of the use levels and a decrease in toxicity of a given agent to the host and the environment. The synergistic activity may be the result of each compound having a different mechanism of action on the target microorganism.

Biocidal combinations, some of which show synergistic activities have been described. Isothiazolones have been combined with: (a) 1-methyl-3,5,7-triaza-1-azonia-tricyclo (3.3.2.2)-decane chloride in U.S. Pat. No. 5,294-614; (b) a heavy metal complex (disodium monocopper (II) citrate) in U.S. Pat. No. 5 4,608,183; (c) hydroxymethylaminoacetic acids, its salts and lower alkyl esters in U.S. Pat. No. 4,980,176; (d) 1,2-benzisothiazolin-3-one in EP No. WO 99/08530; (d) one or more components selected from the group consisting of p-chloro-m-xylenol, sodium dicchlorophene, bis-(2-hydroxy-5-chlorophenyl)sulfide, benzyl-bromoacetate, dodecylamine,4-(2-nitrobutyl) morpholine and dirpopylamine in U.S. Pat. No. 5,489,588; (e) 1,3-dimethylol-5,5-dimethylhydantoin in U.S. Pat. No. 6,114,366, among others. Several of such combinations may exhibit disadvantages, either due to their cost, stability, compatibility, toxicity or other problems.

Isothiazolones also decompose easily and lose their antimicrobial activity, for example, when placed in water or in the presence of other reactive molecules. Dilute solutions of 3-isothiazolones can be stabilized with cationic salts, such as magnesium nitrate or copper nitrate. The use of nitrates as stabilizers is undesirable, however, because of their potential to react with amines and form nitrosamines, which are suspected to be carcinogens.

The stability of 3-isothiazolones can also be improved by the addition of formaldehyde or formaldehyde-donors (U.S. Pat. Nos. 4,129,448, 4,165,318 and 6,121,302). However, these types of stabilizers may also pose a problem. In some animals, formaldehyde may act as a carcinogen.

Other methods have been described to stabilize 3-isothiazolone solutions including U.S. Pat. Nos. 5,461,150 and 5,153,213, which provide methods for stabilizing solutions of 3-isothiazolone by the use of low levels of copper ion in the form of a copper salt (e.g. copper sulfate) or the use of inorganic oxidants (e.g. peroxide). Copper salts may present a problem in those applications, which are sensitive to the addition of salts containing divalent ions. Copper reacts with many anionic surfactants and forms insoluble organic salts, which cause the surfactants to lose function and may result in changes to the physical properties of the finished product. Copper is also a heavy metal, which may pollute the environment.

It is an object of the present invention to provide a synergistic biocidal combination, which is more efficacious than known microbicidal compositions and is also stable in aqueous solutions, thus overcoming the various problems described in the prior art.

SUMMARY OF THE INVENTION

It has been found that a composition comprising a mixture of 2-propenal polymer and isothiazolones exhibits synergistic antimicrobial activity against a wide range of microorganisms; the biological activity of the compounds acting together being greater than the sum of each compound acting alone. Such combination thus presents several advantages, including the use of lesser quantities of active components and an increased level of effectiveness.

The synergistic composition serves to stabilize CIT//MIT in the absence of nitrate salts, formaldehyde, copper salts or inorganic oxidants. Thus, there is provided a formulation that is less-toxic and more compatible with an array of industrial products including architectural coating applications, such as paints and stains; other coating related materials, such as adhesives, sealants, joint compounds, and latex emulsions; and masonry products, wood preservatives, metal working fluid, and water treatment.

DETAILED DESCRIPTION OF THE INVENTION

The present invention is directed to a mixture of biocides designed to control unwanted microbial growth in water-based applications, including, but not limited to, paints and coatings, adhesives, sealants, latex emulsions, joint compounds and masonry products, wood preservation, metal working fluid, and water treatment. The liquid biocidal composition of the present invention comprises a mixture of 2-propenal polymer or copolymer (APC) and CIT/MIT in glycol carriers. The weight ratio of APC to CIT/MIT in the composition of the present invention ranges from about 5,000:1 to about 1:1, preferably from about 500:1 to about 1:1 and most preferably from about 30:1 to about 1:1. Exemplary of the glycol carriers which can be employed in the composition and process of the present invention are ethylene glycol, propylene glycol, etc.

The biocidal formulation according to the present invention is prepared by mixing technical grade CIT/MIT in APC-P (2-propenal polymer in propylene glycol, 50% Al), for example: 0.1 to 20 parts of CIT/MIT to 99.9 to 80 parts of APC-P.

The present invention is illustrated by the following examples.

EXAMPLE I

The synergism of the two-component composition of the present invention was demonstrated by testing a wide range of concentrations and ratios of APC and CIT/MIT, as set forth hereafter.

Each component was added individually or in combination to Tryptic Soy Broth (TSB, from Sigma) at the desired concentration. After addition of the components, 100 μl of a suspension of the testing bacteria (*Pseudomonas aeruginosa* ATCC 10145 or *Bacillus subtilis* ATCC 27328) was added to a final concentration of approximately $10^6$ CFU/ml. The inoculated medium was incubated at 32° C. for 2–3 days.

The lowest concentration of each compound or mixtures to inhibit visible growth was taken as the minimum inhibitory concentration (MIC). The MIC was taken as endpoints of activity. End points for the mixtures of compound A (CIT/MIT) and compound B (APC) were then compared with the end points for the pure active ingredient alone. Synergism was determined by a commonly used and accepted method described by Kull A. C,; Eisman, P. C.; Sylwestrowicz, H. D. and Mayer, R. L. 1961. Applied Microbiology, 9:538–541 using the ratio determined by:

$Q_a/Q_A + Q_b/Q_B$ = synergy wherein:

$Q_A$ is the concentration of compound A in parts per million (PPM), acting alone, which produced and end point.

$Q_a$ is the concentration of compound A in PPM, in the mixture, which produced and end point.

$Q_B$ is the concentration of compound B in PPM, acting alone, which produced and end point.

$Q_b$ is the concentration of compound B in PPM, in the mixture, which produced and end point.

When the sum of $Q_a/Q_A + Q_b/Q_B$ is greater than one (1), antagonism is indicated.

When the sum is equal to one additivity is indicated, and when less than one (1), synergism is demonstrated.

The results demonstrating the synergism of these biocidal combinations are shown in Tables I, II, III and IV.

TABLE I

MINIMAL INHIBITORY CONCENTRATION (MIC)
For *Pseudomonas aeruginosa*

| | | $Q_A$ (PPM) | | | | |
|---|---|---|---|---|---|---|
| | | 0 | 0.935 | 1.87 | 3.75 | 7.5 | 15 |
| $Q_B$ (PPM) | 0 | + | + | + | + | + | − |
| | 50 | + | + | + | + | + | |
| | 100 | + | + | + | + | + | |

TABLE I-continued

MINIMAL INHIBITORY CONCENTRATION (MIC)
For *Pseudomonas aeruginosa*

| | $Q_A$ (PPM) | | | | |
|---|---|---|---|---|---|
| | 0 | 0.935 | 1.87 | 3.75 | 7.5 | 15 |
| 250 | + | + | + | + | + | |
| 500 | + | + | + | + | − | |
| 750 | + | + | + | − | − | |
| 1,000 | + | + | + | − | − | |
| 1,500 | + | + | + | − | − | |
| 2,000 | + | + | + | − | − | |
| 2,500 | + | + | − | − | − | |
| 5,000 | − | | | | | |

TABLE II

SYNERGY INDEX
For *Pseudomonas aeruginosa*

| Microorganism | $Q_a$ (PPM) | $Q_b$ (PPM) | $Q_A$ (PPM) | $Q_B$ (PPM) | $Q_a + Q_b$ (PPM) | SI |
|---|---|---|---|---|---|---|
| Bacteria: | 0 | 5000 | 0 | 5000 | 5000 | 1.0 |
| 1. *P. aeruginosa* | 1.87 | 2500 | 15 | 5000 | 2502 | 0.62 |
| | 3.75 | 2000 | 15 | 5000 | 2038 | 0.65 |
| | 3.75 | 1000 | 15 | 5000 | 1038 | 0.45 |
| | 3.75 | 750 | 15 | 5000 | 754 | 0.40 |
| | 7.5 | 1000 | 15 | 5000 | 1008 | 0.70 |
| | 7.5 | 750 | 15 | 5000 | 758 | 0.65 |
| | 7.5 | 500 | 15 | 5000 | 558 | 0.60 |
| | 15 | 0 | 15 | 0 | 15 | 1.0 |

TABLE III

MINIMAL INHIBITORY CONCENTRATION (MIC)
FOR *BACILLUS SUBTILIS*

| | | $Q_A$ (PPM) | | | |
|---|---|---|---|---|---|
| | | 0 | 0.935 | 1.87 | 3.75 | 7.5 |
| $Q_B$ (PPM) | 0 | + | + | + | + | − |
| | 50 | + | + | + | + | |
| | 100 | + | + | + | + | |
| | 250 | + | + | + | + | |
| | 500 | + | + | + | − | |
| | 750 | + | + | + | − | |
| | 1,000 | + | + | + | − | |
| | 1,500 | + | + | + | − | |
| | 2,000 | + | + | + | − | |
| | 2,500 | + | − | − | − | |
| | 5,000 | − | | | | |

TABLE IV

SYNERGY INDEX
FOR *BACILLUS SUBTILIS*

| Microorganism | $Q_a$ (PPM) | $Q_b$ (PPM) | $Q_A$ (PPM) | $Q_B$ (PPM) | $Q_a + Q_b$ (PPM) | SI |
|---|---|---|---|---|---|---|
| Bacteria: | 0 | 5000 | 0 | 5000 | 5000 | 1.0 |
| 2. *B. subtilis* | 0.94 | 2500 | 7.5 | 5000 | 2501 | 0.62 |
| | 1.87 | 2500 | 7.5 | 5000 | 2502 | 0.75 |
| | 3.75 | 2000 | 7.5 | 5000 | 2004 | 0.90 |
| | 3.75 | 1500 | 7.5 | 5000 | 1504 | 0.80 |
| | 3.75 | 1000 | 7.5 | 5000 | 1004 | 0.70 |
| | 3.75 | 750 | 7.5 | 5000 | 754 | 0.65 |

TABLE IV-continued

SYNERGY INDEX FOR BACILLUS SUBTILIS

| Microorganism | $Q_a$ (PPM) | $Q_b$ (PPM) | $Q_A$ (PPM) | $Q_B$ (PPM) | $Q_a + Q_b$ (PPM) | SI |
|---|---|---|---|---|---|---|
| | 3.75 | 500 | 7.5 | 5000 | 504 | 0.60 |
| | 7.5 | 0 | 7.5 | 0 | 7.5 | 1.0 |

The results demonstrate that the combination of CIT/MIT and APC provides synergistic activity against various microorganisms.

EXAMPLE II

The synergy of the two-component composition of the present invention was also demonstrated by testing various formulations containing different ratios of each active ingredient (Table V). Each prepared formulation was serially diluted in TSB. One hundred 100 μl of a suspension of testing bacteria was added to a final concentration of approximately $10^6$ CFU/ml. The inoculated medium was incubated at 32° C. for 2–3 days.

The lowest concentration to inhibit visible growth was taken as the minimum inhibitory concentration (MIC). The MIC's were taken as endpoints of activity. The results are shown in Table VI and VII. The Synergy Index was calculated and is shown in Table VIII.

TABLE V

Formulations

| Sample | Ratio actives A:B |
|---|---|
| I | 1:46 |
| II | 1:83 |
| III | 1:166 |
| IV | 1:333 |

TABLE VI

MIC FOR PSEUDOMONAS AERUGINOSA

| TOTAL PPM of the Mixture | I | II | III | IV |
|---|---|---|---|---|
| 0 | + | + | + | + |
| 250 | + | + | + | + |
| 500 | − | + | + | + |
| 750 | − | − | + | + |
| 1,000 | − | − | − | + |

TABLE VII

MIC FOR BACILLUS SUBTILIS

| TOTAL PPM of the mixture | I | II | III | IV |
|---|---|---|---|---|
| 0 | + | + | + | + |
| 250 | + | + | + | + |
| 500 | − | − | + | + |
| 750 | − | − | − | + |
| 1,000 | − | − | − | + |

TABLE VIII

SYNERGY INDEX

| Microorganism | $Q_a$ (PPM) | $Q_b$ (PPM) | $Q_A$ (PPM) | $Q_B$ (PPM) | $Q_a + Q_b$ (PPM) | SI |
|---|---|---|---|---|---|---|
| Bacteria: | 0 | 5000 | 0 | 5000 | 5000 | 1.0 |
| 3. P. aeruginosa | 6 | 994 | 15 | 5000 | 1000 | 0.60 |
| | 9 | 741 | 15 | 5000 | 750 | 0.74 |
| | 10 | 490 | 15 | 5000 | 500 | 0.76 |
| | 15 | 0 | 15 | 0 | 15 | 1.0 |
| 4. B. subtilis | 0 | 5000 | 0 | 5000 | 5000 | 1.0 |
| | 5 | 745 | 7.5 | 5000 | 750 | 0.81 |
| | 6 | 494 | 7.5 | 5000 | 500 | 0.90 |
| | 7.5 | 0 | 7.5 | 0 | 7.5 | 1.0 |

EXAMPLE III

The stability of the present invention was demonstrated by adding 11 g (or 1.5 g) of technical CIT/MIT (from SK Chemicals) to 89 g (or 98.5 g) of APC-EG (2-propenal copolymer in ethylene glycol, 50% Al; from Degussa.); a solution was obtained by stirring. The resulting solution was then heated for 25 days at 50° C. Levels (%) of CIT/MIT before and after heat-aging were determined by HPLC with UV detection. The results are shown in Table IX.

TABLE IX

| | % CIT/MIT | |
|---|---|---|
| Sample | Before Heat Aging | Heat Aged (25 days @ 50° C.) |
| CIT/MIT (10.8%) in EG | 9.7/2.7 | 1.89/2.68 |
| CIT/MIT (10.6%) + APC in EG | 9.47/2.66 | 9.23/2.71 |
| CIT/MIT (1.5%) in EG | 2.94/0.35 | 0.43/0.3 |
| CIT/MIT (1.5%) + APC in EG | 2.79/0.35 | 2.57/0.30 |

These data demonstrate that in the presence of APC, there are no significant differences in CIT/MIT levels before and after heat aging. If instead, the same quantities of CIT/MIT are added directly to ethylene glycol, a significant drop in CIT/MIT levels are observed.

What is claimed is:

1. A method of stabilizing a mixture of CIT and MIT to prevent its decomposition and loss of antimicrobial activity, which comprise adding to said CIT/MIT mixture a stabilizing effective quantity consisting of 2-propenal polymer or copolymer (APC).

2. The method according to claim 1, wherein the weight ratio of APC to CIT/MIT is from about 5,000:1 to about 1:1.

3. The method according to claim 1, wherein the weight ratio of APC to CIT/MIT is from about 500:1 to about 1:1.

4. The method according to claim 1, wherein the weight ratio of APC to CIT/MIT is from about 30:1 to about 1:1.

* * * * *